United States Patent [19]

Kondo et al.

[11] Patent Number: 4,643,028

[45] Date of Patent: Feb. 17, 1987

[54] PHASING CIRCUIT FOR USE IN A SCANNING TYPE ULTRASONIC EQUIPMENT

[75] Inventors: Toshio Kondo, Kunitachi; Masao Kuroda, Matsudo, both of Japan

[73] Assignee: Hitachi Medical Corporation, Tokyo, Japan

[21] Appl. No.: 710,388

[22] Filed: Mar. 11, 1985

[30] Foreign Application Priority Data

Mar. 19, 1984 [JP] Japan .................................. 59-53328

[51] Int. Cl.[4] ............................................ G01N 29/00
[52] U.S. Cl. ...................................... 73/625; 310/319; 367/105; 73/626
[58] Field of Search ......................... 73/625, 626, 628; 310/319; 367/105

[56] References Cited

U.S. PATENT DOCUMENTS

| | | | |
|---|---|---|---|
| 4,257,271 | 3/1981 | Glenn | 73/626 |
| 4,392,379 | 7/1983 | Yamaguchi | 73/626 |
| 4,481,823 | 11/1984 | Alais | 73/626 |
| 4,528,854 | 7/1985 | Shimazaki | 73/626 |

*Primary Examiner*—Howard A. Birmiel
*Attorney, Agent, or Firm*—Antonelli, Terry & Wands

[57] ABSTRACT

In the scanning type ultrasonic equipment provided with a probe a plurality of transducer elements and with a phasing circuit for signals which are delivered from the transducer elements on the basis of a received ultrasonic wave, the phasing circuit includes constant current circuits each for converting selected ones of the signals from the transducer elements into a constant current signal, and a delay line having taps which are connected to the constant current circuits, in order to reduce the number of parts included in the phasing circuit and the number of adjusting operations performed therein.

2 Claims, 20 Drawing Figures

NUMBERS OF TRANSDUCER ELEMENTS
DRIVEN IN THIS ORDER

PHASING CIRCUIT FOR USE IN A SCANNING TYPE ULTRASONIC EQUIPMENT

BACKGROUND OF THE INVENTION

The present invention relates to an ultrasonic equipment, and more particularly to a phasing circuit for signals derived from a received ultrasonic wave used in a scanning type ultrasonic equipment provided with a probe including a plurality of transducer elements and with a phasing circuit for signals caused by a received ultrasonic wave, such as an ultrasonic diagnostic equipment of electric sector scanning type.

The ultrasonic diagnostic equipment of electronic sector scanning type uses a probe such as shown in FIG. 1. That is, a probe P includes a plurality of transducer elements B juxtaposed on a sound absorbing material A, and the number of juxtaposed transducer elements per unit length is made as large as possible, to generate an ultrasonic beam having good directional characteristics.

Further, in order to emit an ultrasonic beam in a desired direction, pulse generators connected to the probe P are constructed such that they are connected to counters, the number of which is equal to the number of transducer elements, and that the timing of driving each transducer element is controlled by a train of pulses generated by a corresponding one of the counters. When formed of an integrated circuit, such a pulse generator can be made small in size and low in cost. (Reference may be made to a Japanese Patent Application Specification Publication No. 42293/81).

Recently, in order to make the above pulse generator more small-sized and inexpensive, a custom gate array LSI is used for forming the pulse generator, in place of a general-purpose integrated circuit.

Now, turning to the ultrasonic wave receiving section, analog signals are delivered from the transducer elements on the basis of a received ultrasonic wave, and a variable delay circuit which is complicated, large-sized and expensive, is required to delay the received signals from each transducer element in accordance with desired directional characteristics of the probe in a received ultrasonic wave.

In order to delay the signals from the transducer elements in accordance with the direction of the directional characteristic of the probe in the received ultrasonic wave, and to make small the number of parts included in the delay circuit, it has been proposed to use a phasing circuit such as shown in FIG. 2. In this phasing circuit, as shown in FIG. 2, input terminals ①, ②, ... and ⓝ of delay circuits 1, each of which is formed of a lumped constant type LC delay line having taps, are applied with voltage signals from transducer elements $B_1$, $B_2$, ... and $B_n$ (not shown), respectively. Each delay circuit 1 has a structure shown in FIG. 3. That is, a delay line is made up of a number of inductors L and capacitors C, and taps $T_1$, $T_2$, ... and $T_n$ of the delay line are connected to electronic switches $S_1$, $S_2$, ... and $S_n$, respectively. Thus, the delay time of the delay line can be controlled in such a manner that one of the taps is selected by turning on a corresponding one of the electronic switches. Each delay circuit 1 is used to obtain a relatively short delay time. Incidentally, in FIG. 3, reference character R designates resistors, and reference numeral 5 an amplifier.

Referring back to FIG. 2, the output voltages of one set of three delay circuits 1 are applied to one of adders 2, to be added to each other. The output voltage of each adder 2 is applied to one of delay circuits 3 each having a long delay time, to be delayed by a predetermined time. The output voltages of the delay circuits 3 are applied to an adder 4, to be added to each other. A maximum delay time obtained by the delay circuit 1 is dependent upon a delay time between adjacent ones of the taps $T_1$, $T_2$, ... and $T_n$ of the delay line, and the delay time between adjacent taps is the resolution of the delay circuit 3. In other words, the delay time resolution of the variable delay circuit shown in FIG. 2 is given by the delay time resolution of the delay circuit 1, that is, the delay time between adjacent taps of the delay line shown in FIG. 3.

FIG. 4 shows a delay time which is given to each of the signals from the transducer elements $B_1$ through $B_n$ when an ultrasonic beam has been deflected by an angle of $\theta$, and shows how the delay time is allotted to the delay circuits 1 and 3. Referring to FIG. 4, periods $t_{12}$, $t_{13}$ ... and $t_{19}$ are given by the delay circuits 1, and periods $t_{32}$ and $t_{33}$ are given by the delay circuits 3. For instance, the signal voltages from the transducer elements $B_4$, $B_5$ and $B_6$ are applied to the delay circuits 1, to be delayed by the periods $t_{14}$, $t_{15}$ and $t_{16}$, respectively. The signal voltages thus delayed are added to each other, and the resultant signal thus obtained is applied to the delay circuit 3, to be delayed by the period $t_{32}$.

According to the above system, the number of delay circuits which are required for giving long delay periods to the signal voltages, is equal to one-third the number of delay circuits required in the case where the signal voltages from the transducer elements $B_1$ through $B_n$ are individually given long delay periods. That is, the above system can make the phasing circuit small in size and low in cost.

Further, the number of delay circuits 3 can be reduced by increasing the number of delay circuits 1 connected to one adder 2. In this case, however, the delay time of the delay circuit 1 becomes long, and it is required to increase the taps of the delay line shown in FIG. 3, in order not to reduce the delay time resolution. Accordingly, the number of delay circuits 3 is determined on the basis of a desired delay time resolution and a required limit of cost.

In addition to the phasing circuit shown in FIGS. 2 to 4 for delayinq signal voltages which result from a received ultrasonic wave, such a circuit as shown in FIG. 5 has been proposed. (Refer to the 'Proceedings of the Japan Society of Ultrasonics in Medicine', May, 1976, page 111, and a Japanese Patent application Laid-open No. 102621/77.)

In FIG. 5, reference character 5' designates amplifiers for amplifying signals from transducer elements $B_l$ through $B_n$ of a probe, and S a switching circuit for selecting one of two connection modes; in one connection mode, the signals from terminals ①, ②, ... and ⓝ are sequentially supplied to output terminals $O_1$, $O_2$, ... $O_n$, respectively, in that order, and in another connection mode, the signals from the terminals ①, ②, ... and ⓝ are sequentially supplied to the output terminals $O_n$, $O_{n-1}$, ... and $O_1$, respectively, in that order. Output signals from the output terminals are applied to a circuit made up of delay lines 1' and adders 2'. Thus, the signals from the terminals ① through ⓝ are successively added to each other, after each of these signals having been delayed by a predetermined time. The delay time giving each of the signals at each delay line 1' can be varied in such a manner that one of taps included in the delay line is selected by a control signal CS.

Further, a phasing circuit which is somewhat different in technical thought from but similar in circuit construction to the circuit of FIG. 5, has been proposed. This phasing circuit also uses an LC delay line with taps. (Refer to IEEE, Ultrasonic Symposium, 1980, page 757.)

In the case where a probe having a diameter of about 16 mm includes 48 or 64 transducer elements, the delay system shown in FIG. 2 usually includes 12 or 20 delay lines each having a delay time of 4 to 5 nsec. When an ultrasonic wave having a frequency of 2 to 3.5 MHz is generated and utilized, a ratio of the size of the delay lines to that of the ultrasonic equipment and a ratio of the cost of the delay lines to that of the ultrasonic equipment become large. Accordingly, it is difficult to make the ultrasonic equipment small in size and low in cost.

SUMMARY OF THE INVENTION

An object of the present invention is to provide a small-size and low cost phasing circuit for signals derived from a received ultrasonic wave for use in a ultrasonic equipment which includes a probe having a plurality of transducer elements.

Another object of the present invention is to provide ultrasonic diagnostic equipment of electronic scanning type which includes a small-sized, inexpensive phasing circuit.

According to one aspect of the present invention, in an ultrasonic equipment comprising a probe having a plurality of transducer elements and a phasing circuit for signals derived from a received ultrasonic wave, a tapped delay line each end of which is terminated with a resistor and means for driving the taps with constant current signal source consisting of current mirror circuit or emitter followers with common collector connection corresponding to the signals from the transducer elements are provided in the phasing circuit, to thereby make the phasing circuit small in size and low in cost.

The above and other objects, featurds and advantages of the present invention will be apparent from the following detailed description taken in conjunction with the accompanying drawings.

DESCRIPTION OF THE PREFERRED EMBODIMENTS

Figure 6:
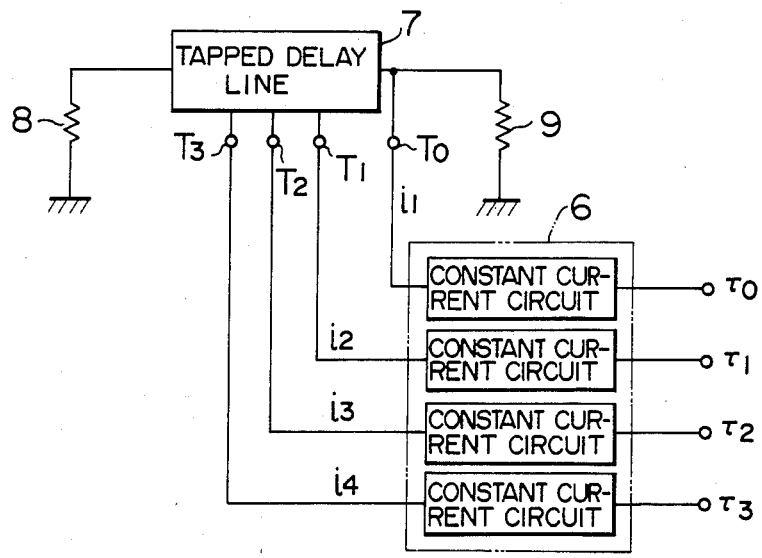
FIG. 6 is a schematic diagram of a delay circuit according to the present invention.

First, the principle of operation of the present invention will be explained hereinbelow with reference to FIG. 6. FIG. 6 is a schematic diagram of a variable delay circuit according to the present invention. According to this delay circuit, an any desired delay time can be added by a single delay line to each of the signal voltages to be added thereafter.

Referring to FIG. 6, let us assume the following. That is, a signal which is derived from a received ultrasonic wave and applied to a tap $T_0$, is given no delay, a signal applied to a tap $T_1$ is given a delay time $\tau_1$, a signal applied to a tap $T_2$ is given a delay time $\tau_2$, and a signal applied to a tap $T_3$ is given a delay time $\tau_3$. Further, in FIG. 6, reference numeral 6 designates constant current circuits, each of which converts a signal derived from the received ultrasonic wave into a constant current, and 7 a delay line having taps. Both ends of the delay line 7 are grounded through terminating resistors 8 and 9, and the resistance of each of the resistors 8 and 9 is equal to the characteristic impedance $Z_0$ of the delay line 7.

The delay line 7 is constructed so that the delay time $\tau_1$ is obtained between the taps $T_0$ and $T_1$, the delay time $\tau_2$ is obtained between the taps $T_0$ and $T_2$, and the delay time $\tau_3$ is obtained between the taps $T_0$ and $T_3$. Accordingly, when constant current signals applied to the taps $T_0$, $T_1$, $T_2$ and $T_3$ are expressed by $i_1(t)$, $i_2(t)$, $i_3(t)$ and $i_4(t)$, respectively, a signal voltage $e_0$ appearing on the tap $T_0$ is given by the following equation:

$$e_0 = \{i_1(t) + i_2(t-\tau_1) + i_3(t-\tau_2) + i_4(t-\tau_3)\tau Z_0 \quad (1)$$

Figure 1:
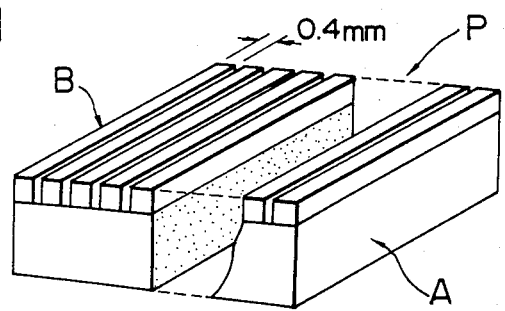
FIG. 1 is a schematic view showing a probe which is used in ultrasonic equipment such as an ultrasonic diagnostic equipment of electronic sector scanning type.
Figure 2:
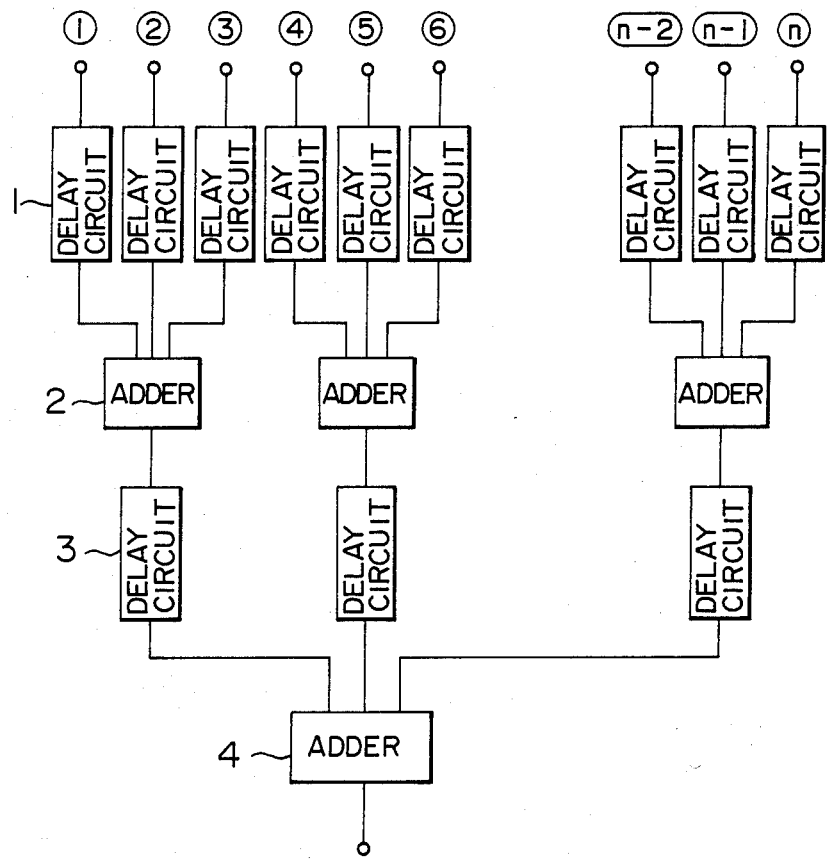
FIG. 2 is a block diagram showing the circuit configuration of a phasing circuit.
Figure 3:
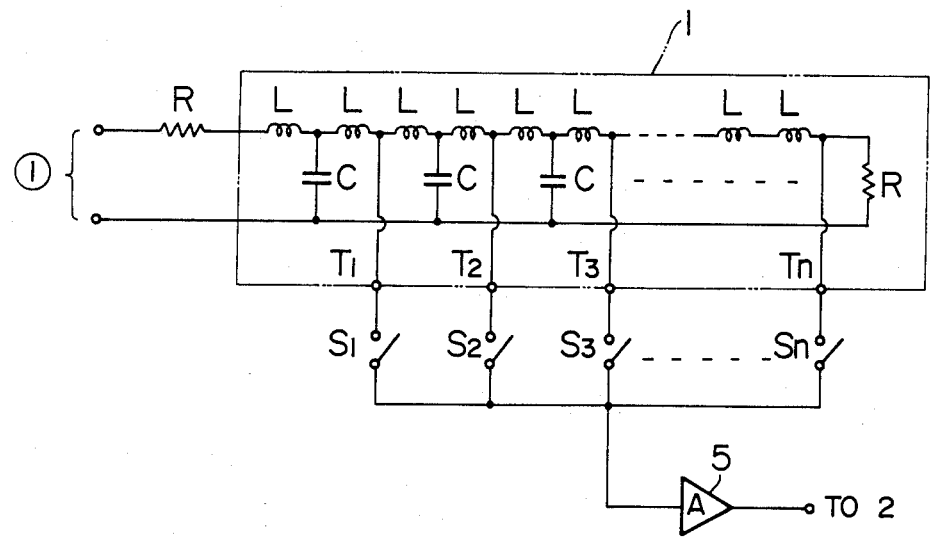
FIG. 3 is a circuit diagram showing the delay circuit of FIG. 2 in detail.
Figure 4:
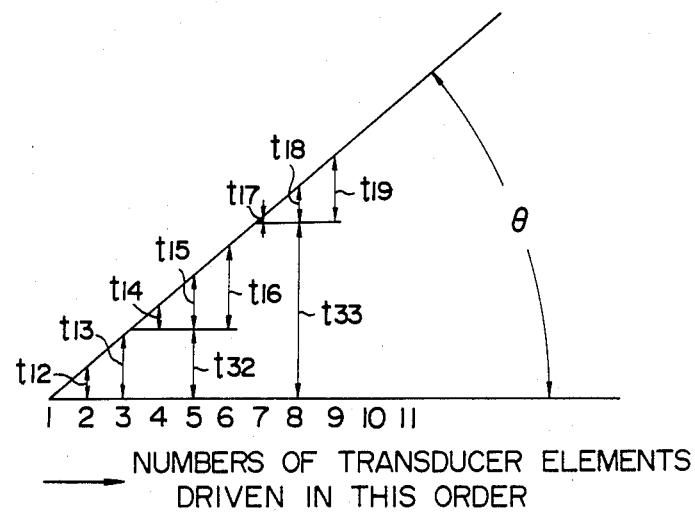
FIG. 4 is a graph showing how a delay time is allotted to the delay circuits 1 and 3 of FIG. 2.
Figure 5:
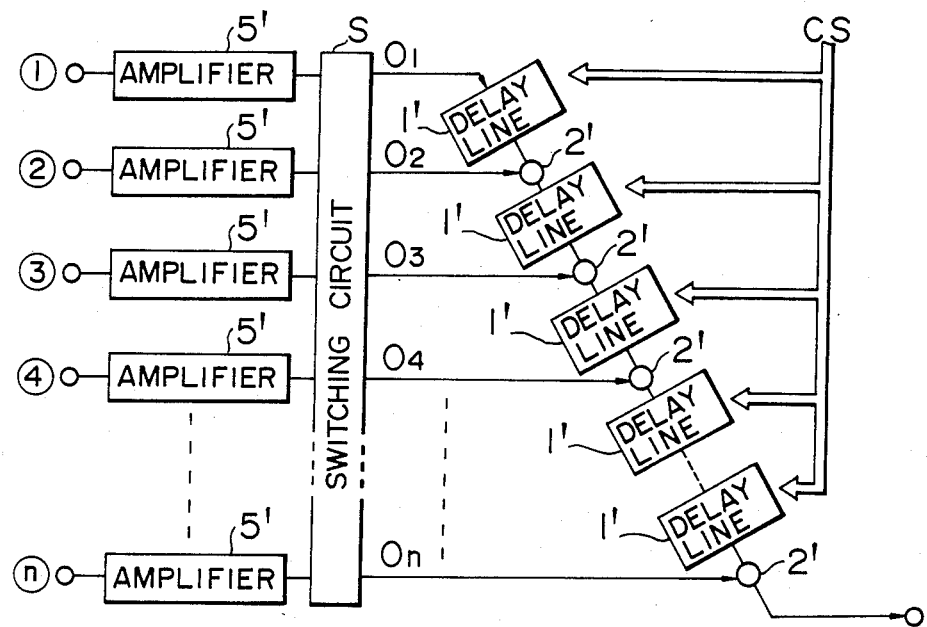
FIG. 5 is a block diagram showing the circuit configuration of a conventional phasing circuit.

It is to be noted that signal voltages which are delivered from transducer elements on the basis of the received ultrasonic wave, are converted by the constant current circuits 6 into the constant current signals $i_1(t)$, $i_2(t)$, $i_3(t)$ and $i_4(t)$. These constant current signals $i_1(t)$, $i_2(t)$, $i_3(t)$ and $i_4(t)$ are applied to the taps $T_0$, $T_1$, $T$ and $T_3$, respectively, and thus the signal voltages $e_0$ given by the equation (1) is obtained at the tap $T_0$. That is, the delay circuit of FIG. 6 has the same function as the conventional phasing circuit shown in FIG. 2.

The impedance of each constant current circuit 6 viewed from the tap connected thereto is infinite, and therefore the load impedance of each tap is very large. Accordingly, there is no fear of a signal being reflected in the delay line 7, and therefore the waveform of the signal is never distorted. As mentioned above, a phasing circuit for delaying each of a number of signals which are derived from a received ultrasonic wave, by a desired time and for adding the signals thus delayed to each other, can be formed of a signal delay line with taps.

Figure 7:
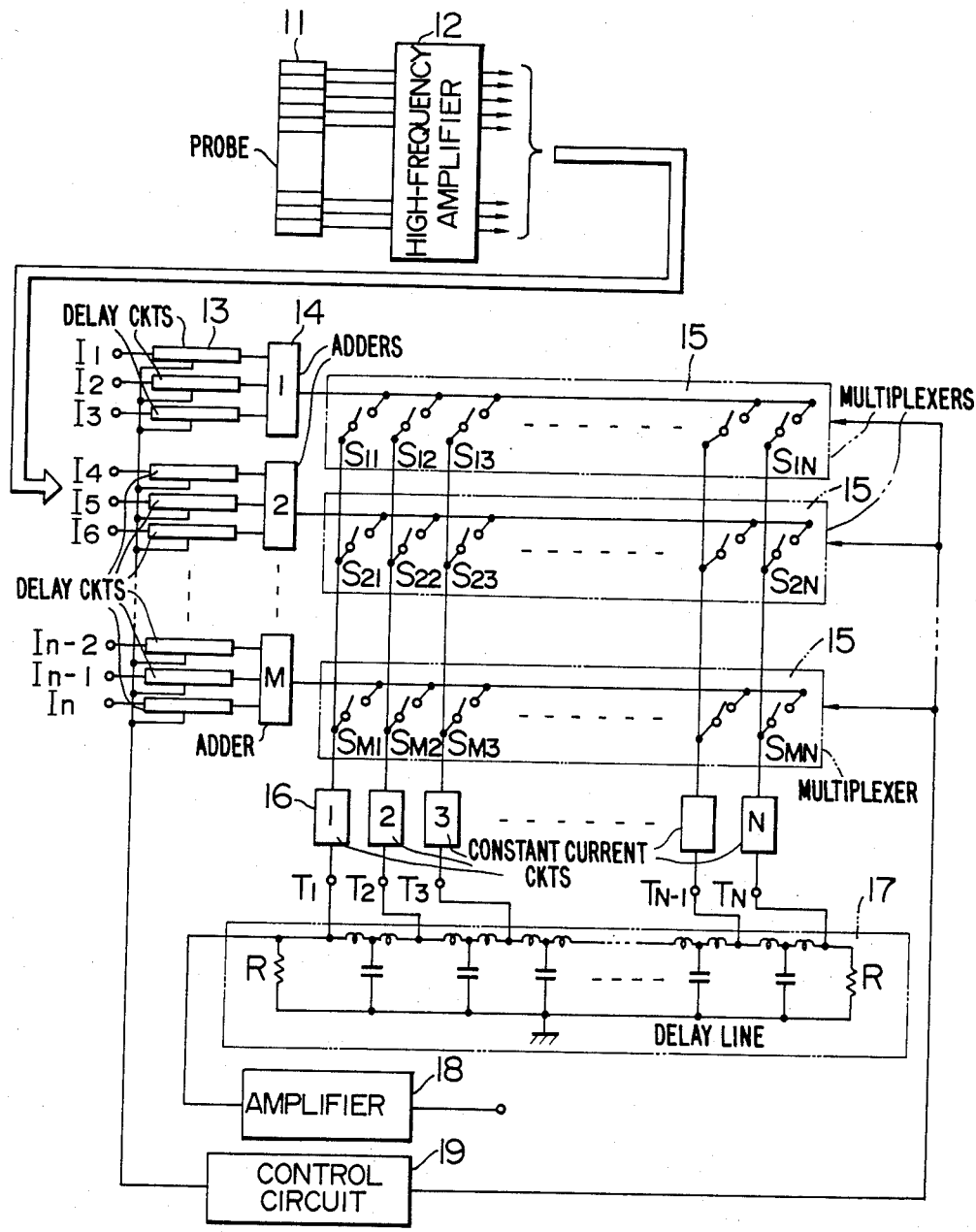
FIG. 7 is a schematic diagram showing an embodiment of an inventive phasing circuit for signals derived from a received ultrasonic wave, and showing a peripheral circuit of the embodiment.

FIG. 7 shows an embodiment of an inventive phasing circuit for signals which are derived from a received ultrasonic wave in the ultrasonic diagnostic equipment of electronic sector scanning type, and shows a peripheral circuit of the embodiment. In FIG. 7, reference numeral 11 designates a probe in which n long and narrow transducer elements are juxtaposed on a sound absorbing material, 12 an n-channel high-frequency amplifier, 13 an n-channel delay circuit, 14 adders, 15 multiplexers each formed of N electronic switches, 16 constant current circuits, 17 a delay line having N taps, 18 an amplifier, and 19 a control circuit. Further, in FIG. 7, reference symbols $S_{11}$ to $S_{1N}$, $S_{21}$ to $S_{2N}$, ... and $S_{M1}$ to $S_{MN}$ designate electronic switches, $T_1$ to $T_N$ taps of the delay line 17, and R resistors each having a resistance equal to the characteristic impedance of the delay line 17.

Next, the operation of the present embodiment will be explained. Referring to FIG. 7, signal voltages which are delivered from the probe 11 on the basis of a received ultrasonic wave, are sent to the n-channel high-frequency amplifier 12, and the amplified signal voltages from the amplifier 12 are applied to input terminals $I_1$ to $I_n$ of the n-channel delay circuit 13. The delay time at each channel of the delay circuit 13 is controlled by a control signal from the control circuit 19. Now, let us assume that a maximum delay time of the delay circuit 13 is $\tau_{om}$ and a minimum controllable delay time resolution of the same is $\Delta\tau_0$. Output voltages from the delay circuit 13 are divided among a plurality of groups, and output voltages contained in one group are applied to one adder 14, to be added to each other. When one group is formed of m channels of the delay circuit 13, the number M of adders 14 is equal to n/m. That is, M output voltages are delivered from the adders 14. Each of the output voltages from the adders 14 is sent to a corresponding one of the multiplexers 15 each having N electronic switches. The electronic switches $S_{11}$ to $S_{1N}$, $S_{21}$ to $S_{2N}$, ... and $S_{M1}$ to $S_{MN}$ are connected in the form of a matrix, as shown in FIG. 7. Thus, the output signals from the adders 14 are applied through the multiplexers 15 to the constant current circuits 16, which act as constant current sources for supplying constant current signals to the taps $T_1$ to $T_N$ of the delay line 17. Network of the constant current circuits 16 and delay line 17 has a function of adding all input signals thereof to each other. The delay time between any adjacent taps is set to be equal to one another throughout the delay line 17, and each of the input and output terminals of the delay line 17 is grounded through the resistor R. As mentioned previously, the resistors R have a resistance equal to the characteritic impedance of the delay line 17. One of the resistors R is connected to the amplifier 18, which has a high input impedance. The output voltage of the amplifier 18 is a summing signal voltage which is phase-adjusted in each channel for an electronic sector scanning operation.

When the maximum delay time $\tau_{om}$ of the delay circuit 13 is made longer than the delay time $\Delta\tau$ which is the delay time between adjacent taps of the delay line 17 and the number M of adders 14 is made equal to the number N of taps of the delay line 17, each of signals applied to the input terminals $I_1$ to $I_n$ of the delay circuit 13 can be given a delay time in a range from zero to $\Delta\tau(N-1)$ by the delay line 17. However, when only input terminals connected to one adder 14, for instance, only the input terminals $I_4$, $I_5$ and $I_6$ are considered, a difference in delay time between the signal applied to one of these input terminals and the signal applied to another one of the input terminals, is less than the maximum delay time $\tau_{om}$ of the delay circuit 13.

In FIG. 7, signals from the three channels of the delay circuits 13 are added to each other by one adder 14, and thus M signals are delivered from the adders 14. Each of M signals is applied to a desired one of N taps of the delay line 17 in the form of a constant current signal. Now, let us consider the case where the number of input terminals of the delay circuit 13 is 48, the maximum delay time $\tau_{om}$ of the delay circuit 13 is 300 nsec, the number N of taps of the delay line 17 is equal to 16, the number M of adders 14 is equal to 16, and the delay time between adjacent taps of the delay line 17 is 300 nsec. Then, the signals applied to the input terminals of the delay circuit 13 can be delayed by a time less than or equal to 4.8 μsec. Further, when a probe having a diameter of about 15 mm and including 48 transducer elements juxtaposed at intervals of about 0.3 mm is used, an ultrasonic beam can be deflected by an angle of ±45°.

Next, the detailed structure of each part of the embodiment shown in FIG. 7 will be explained.

Now, let us suppose that the maximum delay time of the delay circuit 13 is 300 nsec and the frequency of the ultrasonic wave is 3.5 MHz. As is known, when the unit delay time of a phasing circuit is made larger, the performance thereof is deteriorated. (Refer to "Japanese Journal of Medical Ultrasonics", by T. Kondo et al Vol. 4, No. 4, page 290 (1977).) Accordingly, in this case, a delay time far shorter than a time corresponding to one-tenth the wavelength of the ultrasonic wave, for example, 10 nsec is used as the minimum controllable delay time resolution of the delay circuit 13. That is, it is required to make the minimum resolution equal to 10 nsec.

Figure 8:
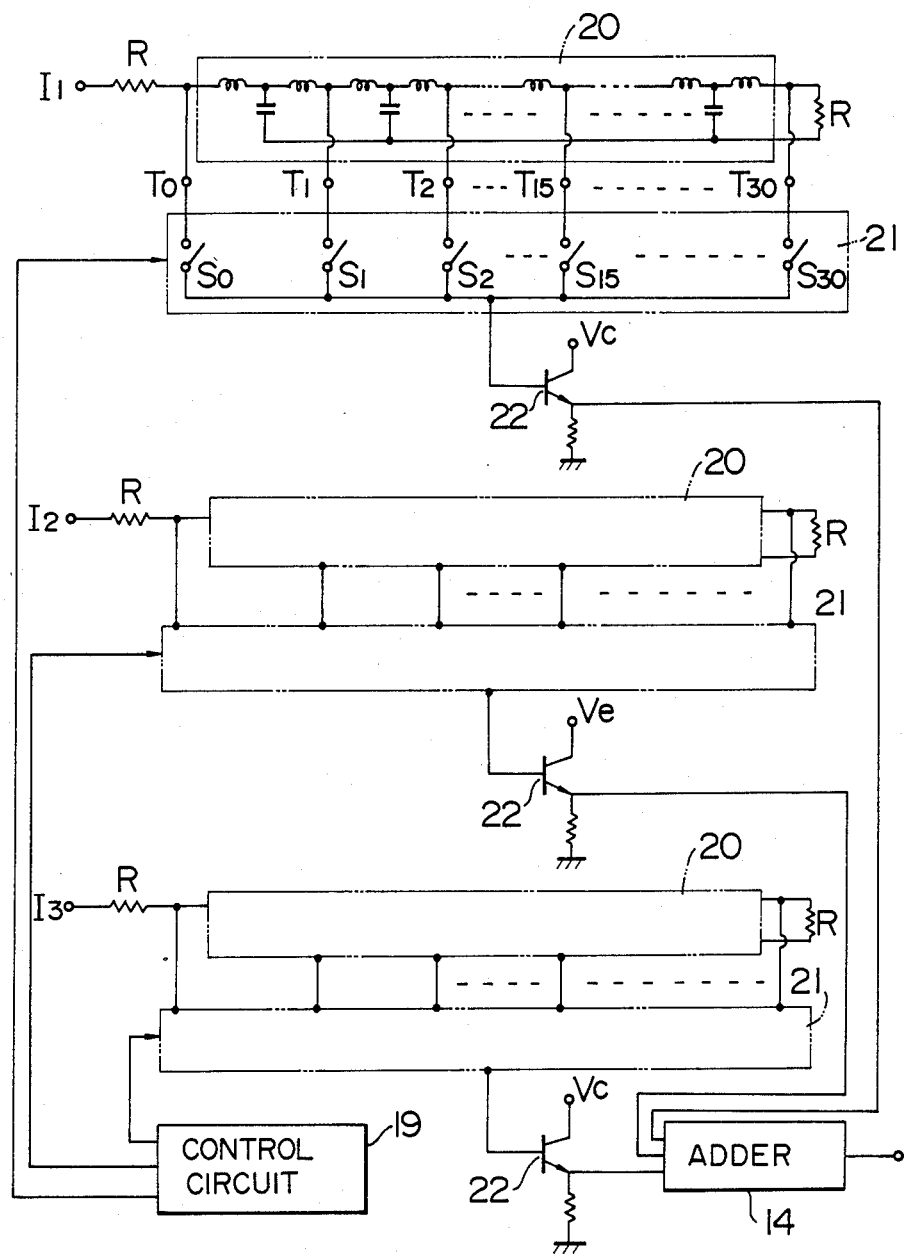
FIG. 8 is a circuit diagram showing an specific example of the delay circuit 13 of FIG. 7.

FIG. 8 shows an example of the delay circuit 13 having a delay time resolution of 10 nsec. In FIG. 8, the same reference symbols as in FIG. 7 designate like parts. Further, in FIGS. 8, 9, 10 and 13, reference symbol $V_c$ designates a constant voltage source.

Referring to FIG. 8, a delay line 20 having taps receives a signal voltage through a resistor having a resistance equal to the characteristic impedance of the delay line 20, and another resistor R having the same resistance as mentioned above is connected to the end of the delay line 20. The delay line 20 has taps $T_0$ to $T_{30}$, and a delay time between adjacent taps is equal to 10 nsec. The taps $T_0$ to $T_{30}$ are connected to electronic switches $S_0$ to $S_{30}$ of a multiplexer 21, respectively, so that any desired delay time selected from 0 nsec, 10 nsec, 20 nsec, ... and 300 nsec can be set by operating these electronic switches $S_0$ to $S_{30}$. In order to prevent a signal voltage which is to be supplied from each of the taps $T_0$ to $T_{30}$ of the delay line 20 to the multiplexer 21, from being distorted in the delay line 20 by characteristic-impedance mismatching, it is required to connect the output side of the multiplexer 21 to an amplifier 22 having a high input impedance. The amplifier 22 can be formed of a simple emitter follower circuit. The signal voltage delivered from the amplifier 22 is applied to the adder 14. The ON-OFF action of each electronic switch included in the multiplexer 21 is controlled on the basis of change-over data stored in a read only memory (ROM) which is provided in the control circuit 19.

Figure 9:
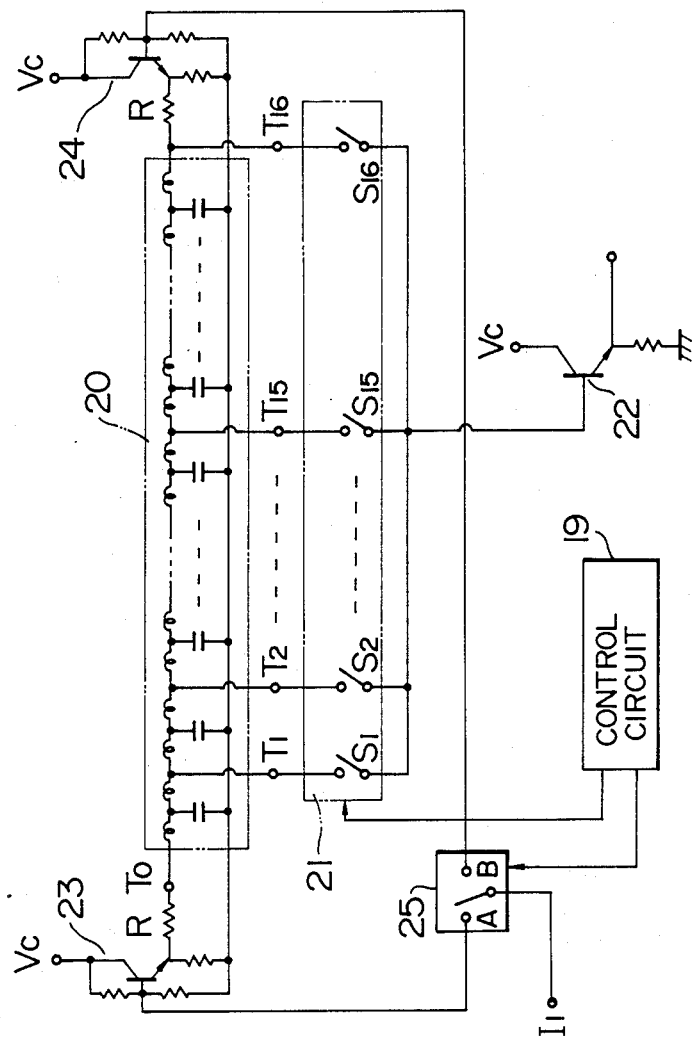
FIG. 9 is a circuit diagram showing another example of the delay circuit 13 of FIG. 7.

FIG. 9 shows another example of the delay circuit 13 of FIG. 7. In FIG. 9, the same reference symbols as in FIG. 8 designate like parts.

Referring to FIG. 9, emitter follower circuits 23 and 24 are applied with a signal voltage from the high-frequency amplifier 12 for amplifying signals which are derived from a received ultrasonic wave received at the transducer elements. When the feedback coefficient $\beta$ of a transistor included in each of the emitter follower circuits 23 and 24 is sufficiently large, the output impedance of each emitter follower circuit is small. Further, input and output terminals of a delay line 20 are connected to the emitter follower circuits 23 and 24 through resistors R, each of which has a resistance equal to the characteristic impedance of the delay line 20. Accordingly, when an electronic switch 25 is set to an A-terminal side, the signal voltage from the high-frequency amplifier 12 is applied to the emitter follower circuit 23, and the delay line 20 is driven from the left-hand side. In this case, the delay line 20 is considered to terminate at a tap $T_{16}$ which is connected to the resistor R. On the other hand, when the electronic switch 25 is set to a B-terminal side, the signal voltage from the high-frequency amplifier 12 is applied to the emitter follower circuit 24, and the delay line 20 is driven from the right-hand side. In this case, the delay line 20 is considered to terminate at a tap $T_0$ which is connected to the resistor R. The delay line 20 has taps $T_1$ to $T_{15}$, in addition to the taps $T_0$ and $T_{16}$, and the taps $T_1$ to $T_{15}$ are provided so that a delay time between adjacent ones of the taps $T_0$ to $T_{15}$ is 10 nsec and a delay time between the taps $T_{15}$ and $T_{16}$ is 150 nsec. The taps $T_1$ to $T_{16}$ are connected to electronic switches $S_1$ to $S_{16}$ included in a multiplexer 21, respectively. Accordingly, when the electronic switch 25 is set to the A-terminal side to drive the delay line 20 from the left-hand side, 16 kinds of delay time (that is, 10, 20, 30, ..., 150 and 300 nsec) can be given to the signal voltage from the high-frequency amplifier 12, by controlling the switching operation of the electronic switches $S_1$ to $S_{16}$. Further, when the electronic switch 25 is set to the B-terminal side to drive the delay line 20 from the right-hand side, 15 kinds of delay time (that is, 0, 150, 160, 170, ... and 290 nsec) can be given to the signal voltage from the high-frequency amplifier 12, by controlling the electronic switches $S_1$ to $S_{16}$ of the multiplexer 21 by the control circuit 19. By using such a circuit configuration, the number of taps of the delay line 20 and the number of electronic switches included in the multiplexer 21 are both halved, as compared with the circuit configuration of FIG. 8.

Figure 10:
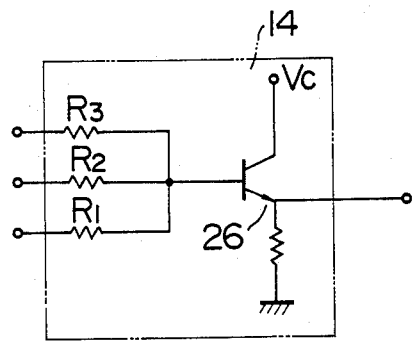
FIGS. 10 and 11 are circuit diagrams showing examples of the adder 14 of FIG. 7.
Figure 11:
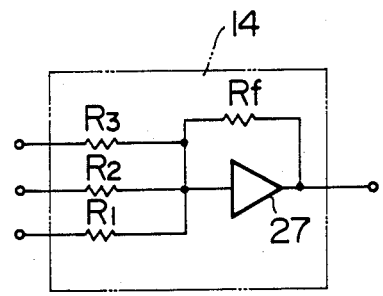

FIGS. 10 and 11 show examples of the adder 14 shown in FIG. 7.

In the example of FIG. 10, resistors $R_1$, $R_2$ and $R_3$ are connected to the base of a transistor which is included in an emitter follower circuit 26. In this example, the amplitude of each of signals applied to the resistors $R_1$, $R_2$ and $R_3$ is reduced to one-third of an original amplitude in output terminal of the emitter follower circuit 26, while, in the example shown in FIG. 11 which is made up of resistors $R_1$, $R_2$, $R_3$ and $R_f$ and an operational amplifier 27, signals applied to the resistors $R_1$, $R_2$ and $R_3$ are added to each other, without being attenuated, where $R_l=R_2=R_3=R_f$.

Referring back to FIG. 7, only the output voltages of adders 14 which voltages are connected to turned on ones of the electronic switches $S_{11}$, $S_{21}$, ... and $S_{M1}$, are added to each other, and then converted into a constant current signal, to be applied to the tap $T_1$ of the delay line 17.

Now, explanation will be made on how the outputs of the adders 14 are added to each other.

Figure 12:
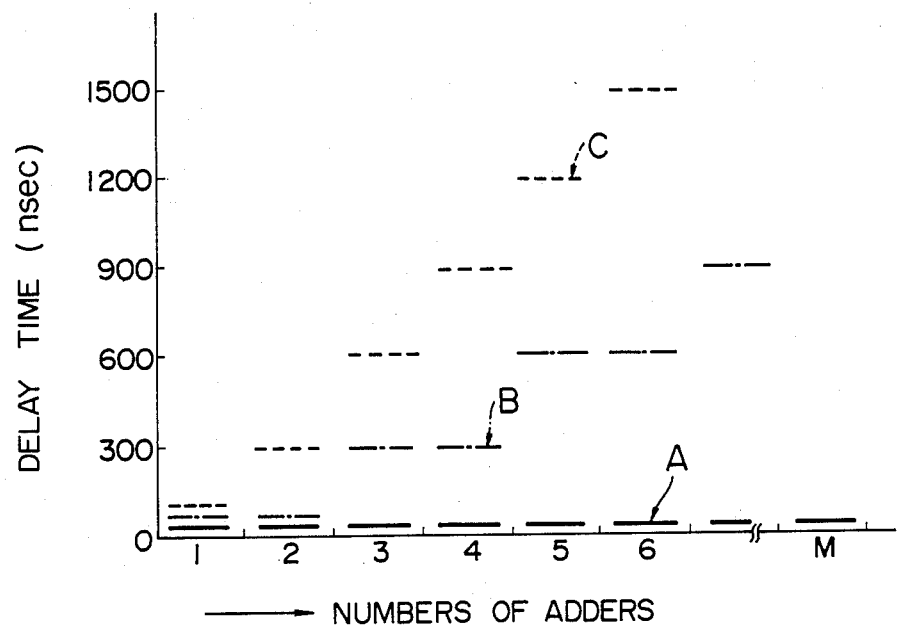
FIG. 12 is a graph showing examples of a delay time which is given to the signal voltage outputted from each adder 14 of FIG. 7.

FIG. 12 shows a delay time which is given to each of the output voltages of the adders 14 by the delay line 17 on the basis of the states of the electronic switches $S_{11}$ to $S_{MN}$.

Referring to FIG. 12, solid lines A indicate a delay time which is given to each of the output voltages of the adders 14 in the case where only the electronic switches $S_{11}$, $S_{21}$, $S_{31}$, ... and $S_{M1}$ are turned on and the remaining electronic switches are turned off, dot-dash lines B indicate a delay time in the case where only the electronic switches $S_{11}$, $S_{21}$, $S_{32}$, $S_{42}$, ... are turned on and the remaining electronic switches are turned off, and broken lines C indicate a delay time in the case where only the electronic switches $S_{11}$, $S_{22}$, $S_{33}$, ... are turned on and the remaining electronic switches are turned off.

It can be seen from FIG. 12 that it is possible to give a desired delay time in units of 300 nsec to the output voltage of each adder 14 and then add them to each other.

Figure 13:
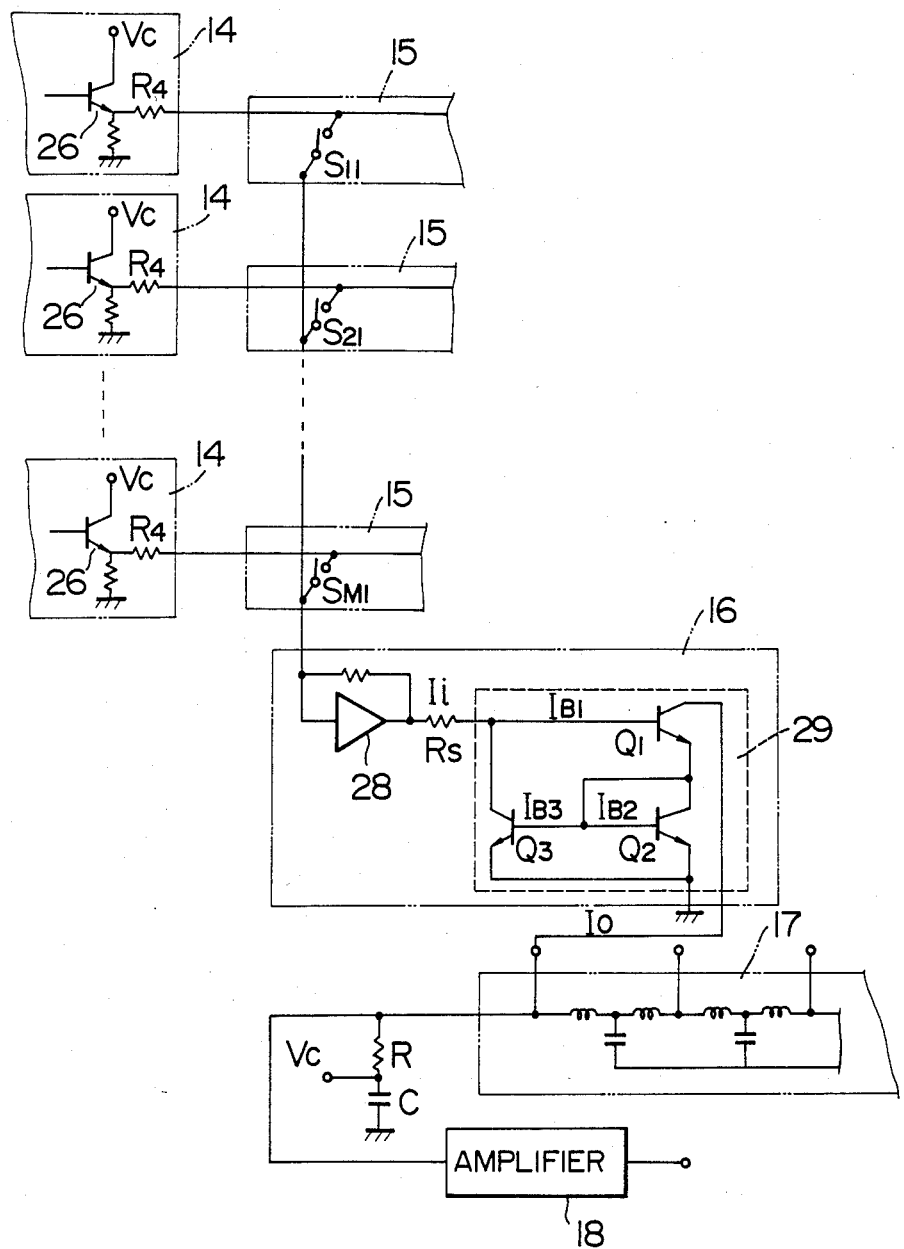
FIG. 13 is a circuit diagram showing an example of a circuit configuration for supplying a constant current signal to each tap of the delay line 17 shown in FIG. 7 according to the present invention.

FIG. 13 shows an example of a circuit configuration for supplying the tap $T_1$ of the delay line 17 with a constant current signal corresponding to the sum of the output voltages of the adders 14. In FIG. 13, the same reference symbols as in FIGS. 7 and 10 designate like parts.

Referring to FIG. 13, the output of the emitter follower circuit 26 included in each adder 14 is connected to a multiplexer 15 through a resistor $R_4$. Signals from the electronic switches $S_{11}$, $S_{21}$, ... and $S_{M1}$ of the multiplexers 15 are applied to the input terminal of an operational amplifier 28 which is included in a constant-current circuit 16. Thus, the output voltages of the adders 14 are added to each other in accordance with the states of the electronic switches $S_{11}$, $S_{21}$, ... and $S_{M1}$, and the result of addition appears on the output terminal of the operational amplifier 28. An output voltage V from the operational amplifier 28 is converted by a current mirror circuit 29 which is made up of transistors $Q_1$, $Q_2$ and $Q_3$, into a constant current signal, which is applied to the tap $T_1$ of the delay line 17. The transistors $Q_2$ and $Q_3$ of the current mirror circuit 29 have the same $V_{BE}-I_{BE}$ characteristic, and moreover the bases of these transistors are connected to each other. Accordingly, the transistors $Q_2$ and $Q_3$ have the same collector current. When the transistors $Q_1$, $Q_2$ and $Q_3$ have the same characteristics, respective base currents $I_{B1}$, $I_{B2}$ and $I_{B3}$ of the transistors $Q_1$, $Q_2$ and $Q_3$ are equal to each other (namely, $I_{CB1}=I_{B2}=I_{B3}$), and the collector currents $I_{C2}$ and $I_{C3}$ of the transistors $Q_2$ and $Q_3$ are equal to each other (namely, $I_{C2}=I_{C3}$). When an input current to the current mirror circuit 29 and a load current thereof are expressed by $I_i$ and $I_0$, respectively, the collector current $I_{C3}$ of the transistor $Q_3$ is given by $I_i-I_{B1}$ (namely, $I_{C3}=I_i-I_{B1}$), while the collector current of the transistor $Q_2$ is given by an equation $I_{c2}=I_0+I_{B1}-I_{B2}-I_{B3}$. Since the collector current $I_{C2}$ is equal to the collector current $I_{C3}$, the load current $I_0$ is expressed as follows:

$$I_0=I_i+(I_{B2}+I_{B3}-2I_{B1})=I_i$$

That is, the load current $I_0$ is equal to the input current $I_i$.

The output impedance of the current mirror circuit 29 can be set in a range from 10 to 1,000 MΩ, or made greater than 1,000 MΩ, while, the delay line 17 has a characteristic impedance of 50 to hundreds of ohms. That is, the impedance of the delay line 17 viewed from each tap is far smaller, as compared with the output impedance of the current mirror circuit 29. In other words, the impedance of the delay line 17 which acts as the load of the current mirror circuit 29, is negligibly small, and thus the waveform of the signal applied to the delay line is never distorted. Further, the input circuit $I_i$ to the current mirror circuit 29 is given by a ratio $V/R_s$, where V indicates the output voltage of the operational amplifier 28, and $R_s$ is the resistance of a resistor $R_s$ connected to the input side of the current mirror circuit 29. Accordingly, the load current (namely, the output current) of the current mirror circuit 29 is also equal to $V/R_s$. It is to be noted that a current flowing through the current mirror circuit 29 is supplied from the constant voltage sources which are connected to terminal resistors R provided at both ends of the delay line 17.

Figure 14:
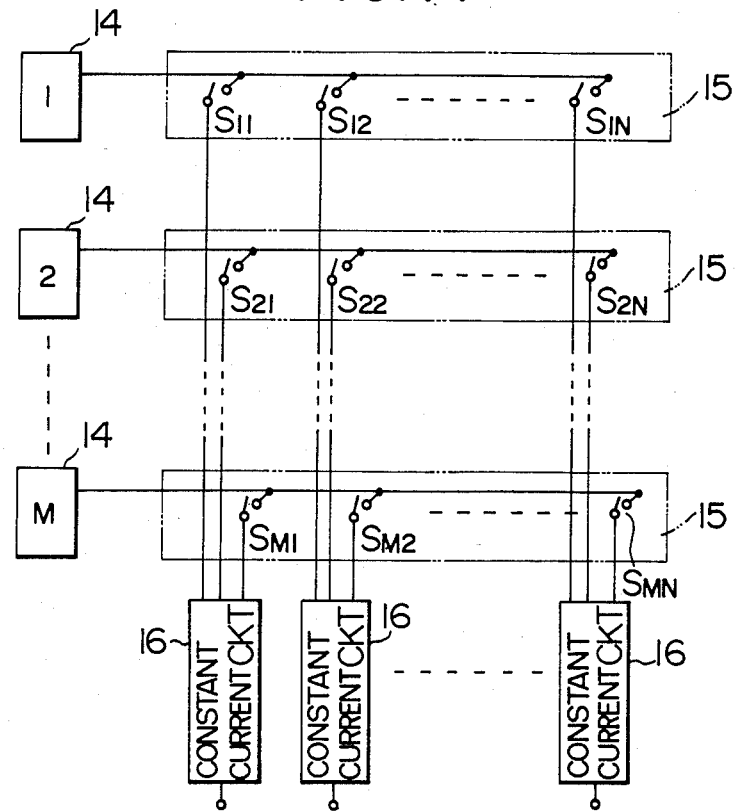
FIG. 14 is a schematic diagram showing another example of a circuit configuration for supplying a constant current signal to each tap of the delay line 17 according to the present invention.

In the circuit construction of FIG. 13, as the constant current circuit 16 which is to be connected to each of the taps $T_1$ to $T_N$ of the delay line 17, the operational amplifier 28 and current mirror circuit 29 are used. However, the constant current circuit is not limited to such a circuit configuration. For example, as shown in FIG. 14, respective output voltages of M adders 14 shown in FIG. 7 may be individually taken out by the electronic switches, and then applied to a constant current circuit 16 having an adding function such as shown in FIG. 15 or 16.

Figure 15:
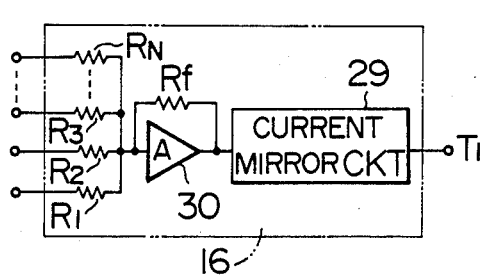
FIGS. 15 and 16 are circuit diagrams showing examples of the constant current circuit 16 of FIG. 14.
Figure 16:
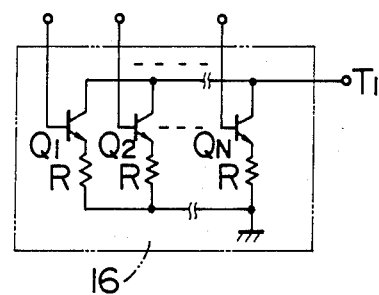

FIGS. 15 and 16 show examples of the above-mentioned constant current circuit 16 having an adding function.

The constant current circuit of FIG. 15 includes resistors $R_1$ to $R_N$, a feedback resistor $R_f$, an operational amplifier 30, and the current mirror circuit 29 of FIG. 13, to have the above-mentioned adding function.

The constant current circuit of FIG. 16 includes N emitter follower circuits connected in parallel. Respective collectors of the transistors $Q_1$ to $Q_N$ included in the emitter follower circuits are connected to each other and further connected to a tap of the delay line 17. Thus, some of the output voltages of M adders 14 are selected by the multiplexers 15, and then added to each other by the constant current circuit. The output of the constant current circuit is applied to the tap in the form of a constant current signal.

Further, in the constant current circuit of FIG. 16, each of the emitter follower circuits including the transistors $Q_1$ to $Q_N$ may be replaced by the current mirror circuit 29 of FIG. 13.

FIGS. 17 to 20 are circuit diagrams showing typical examples of the current mirror circuit, which can be used in a phasing circuit according to the present invention. Now, supplementary explanation will be made on the operation of the current mirror circuit, with reference to FIGS. 17 to 20.

The current mirror circuit is a general term for constant current sources, in which a plurality of transistors having the same characteristics are combined so as to generate a constant current corresponding to an input signal current. A number of transistors having the same characteristics can be formed in an integrated circuit.

Accordingly, in recent years, the current mirror circuit has been used widely in various ICs and various kinds of current mirror circuits have been proposed.

Now, typical examples of the current mirror circuits and the operation thereof will be explained below.

Figure 17:
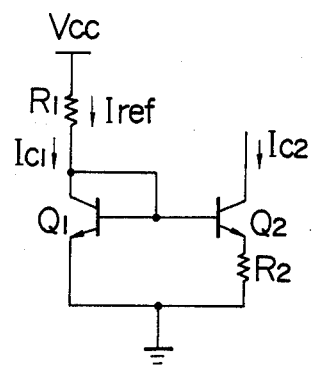
FIGS. 17 to 20 are circuit diagrams showing current mirror circuits usable in a phasing circuit according to the present invention.

A current source shown in FIG. 17 is called "Wildlar current source". The operation of this current source will first be explained.

When the collector-emitter voltage and emitter-base voltage of a transistor is expressed b $V_{CE}$ and $V_{BE}$, respectively, the collector current $I_C$ of the transistor is generally given by the following equation:

$$I_C = I_S \left( \exp \frac{V_{BE}}{V_T} \right) \left( 1 + \frac{V_{CE}}{V_A} \right) \quad (2)$$

where $I_S$, $V_T$ and $V_A$ are constants.

Further, in the current source of FIG. 17, the following equation is obtained:

$$V_{BE1} - V_{BE2} - I_{C2}R_2 = 0 \quad (3)$$

When $V_A \gg 1$, the following equation is obtained from the equations (2) and (3):

$$V_T \ln \frac{I_{C1}}{I_{S1}} - V_T \ln \frac{I_{C2}}{I_{S2}} - I_{C2}R_2 = 0 \quad (4)$$

When transistors $Q_1$ and $Q_2$ shown in FIG. 17 have the same characteristics, $I_{S1}$ is equal to $I_{S2}$. Accordingly, the equation (4) is rewritten as follows:

$$V_T \ln \frac{I_{C1}}{I_{C2}} = I_{C2}R_2 \quad (2)$$

Thus, when the resistance $R_2$ and collector current $I_{C1}$ are given, the collector current $I_{C2}$ is constant independently of the collector voltage of the transistor $Q_2$. That is, the output current $I_{C2}$ of the current source shown in FIG. 17 is determined by the input current $I_{C1}$ thereof.

Figure 18:
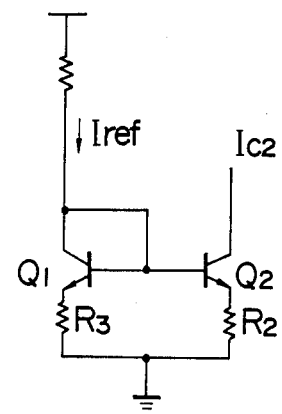
Figure 19:
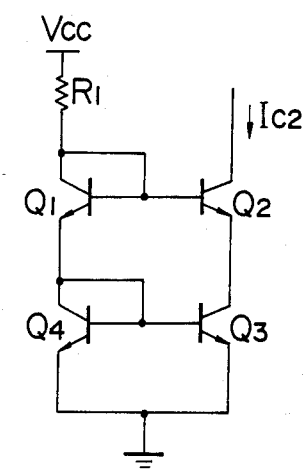

FIGS. 18 and 19 show a simple current source and a cascade current source which have been proposed on the basis of the current source of FIG. 17.

Figure 20:
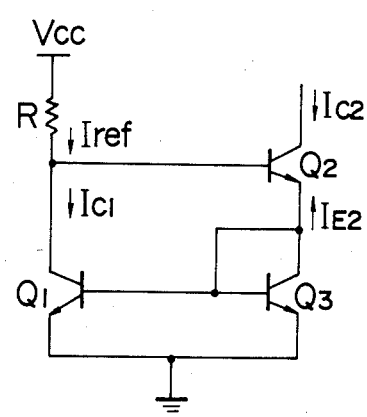

Further, a current source has been devised which is shown in FIG. 20. This current source is called "Wilson current source", and has a large output impedance in spite of a relatively simple circuit structure. Of these current sources, the Wilson current source is most widely used. For the current source of FIG. 20, the following equations are obtained:

$$-I_{E2} = I_{C3} + I_{B3} + I_{B1} = I_{C3}\left(1 + \frac{1}{\beta_F}\right) + \frac{I_{C1}}{\beta_F} \quad (6)$$

$$-I_{E2} = I_{C3}\left(1 + \frac{2}{\beta_F}\right) \quad (7)$$

where $\beta_F$ indicates the current amplification factor of transistor.

Further, the following equation is obtained:

$$I_{C2} = -I_{E2}\left(\frac{\beta_F}{1+\beta_F}\right) = I_{C3}\left(1 + \frac{2}{\beta_F}\right)\left(\frac{\beta_F}{1+\beta_F}\right) \quad (8)$$

The equation (8) can be rewritten as follows:

$$I_{C3} = I_{C2}\left[\frac{1}{\left(1+\frac{2}{\beta_F}\right)\left(\frac{\beta_F}{1+\beta_F}\right)}\right] \quad (9)$$

Further, a collector current $I_{C1}$ is given by the following equation:

$$I_{C1} = I_{ref} - \frac{I_{C2}}{\beta_F} \quad (10)$$

When $\beta_F >> 1$, $I_{C1} = I_{C3}$ (11)

From the equations (9), (10) and (11), we can obtain the following equations:

$$I_{C2} = I_{ref}\left(1 - \frac{2}{\beta_F^2 + 2\beta_F + 2}\right) \quad (12)$$

That is, the current $I_{C2}$ corresponds to the input current $I_{ref}$ with an error of about $2/\beta_F^2$. Further, the output impedance $R_0$ of the current source of FIG. 20 can be calculated and is given as follows:

$$R_0 \approx \beta_F r_{o2}/2$$

where $r_{o2}$ indicates the output resistance of a transistor.

As is apparent from the above equation, the output resistance $R_0$ of the current source shown in FIG. 20 is $\beta_F/2$ times larger than the output resistance of the transistor.

As has been explained in the foregoing, according to the present invention, a plurality of delay circuits included in a phasing circuit are replaced by a single delay/addition circuit, and therefore it is possible to make small the size of electronic scanning type ultrasonic equipment provided with a probe having a plurality of transducer elements and with a phasing circuit for signals caused by a received ultrasonic wave such as the ultrasonic diagnostic equipment of electronic scanning type.

Further, the number of parts included in the phasing circuit and the number of adjusting operations required in the phasing circuit are greatly reduced. Thus, not only the phasing circuit but also the ultrasonic equipment becomes low in cost.

Furthermore, since a phasing circuit according to the present invention is small in size, the transducer elements included in the probe can be greatly increased to improve the performance of the ultrasonic equipment.

Although a preferred embodiment of a phasing circuit according to the present invention has been explained, the present invention is not limited to such an embodiment, but various changes and modifications can be made without departing from the spirit and scope of the invention.

Needless to say, the present invention is also applicable to ultrasonic equipment of electronic linear scanning type or mechanical scanning type using an annular array probe.

We claim

1. In a scanning type ultrasonic equipment including a probe having a plurality of transducer elements and a phasing circuit for signals which are delivered from said transducer elements on the basis of a received ultrasonic wave, said phasing circuit comprising a constant current circuit for converting said signals from said transducer elements into a constant current signals, and a delay line having taps and driven by said constant current signal from said constant current circuit, said constant current circuit including a current mirror circuit.

2. In a scanning type ultrasonic equipment including a probe having a plurality of transducer elements and a phasing circuit for signals which are delivered from said transducer elements on the basis of a received ultrasonic wave, said phasing circuit comprising a constant current circuit for converting said signals from said transducer elements into a constant current signals, and a delay line having taps and driven by said constant current signal from said constant current circuit, said constant current circuit including a plurality of emitter follower circuits whose collectors are connected to each other, to have an adding function.

* * * * *